United States Patent
Su et al.

(10) Patent No.: US 9,335,443 B2
(45) Date of Patent: *May 10, 2016

(54) ANTI-REFLECTIVE LENSES AND METHODS FOR MANUFACTURING THE SAME

(71) Applicant: QSpex Technologies, Inc., Alpharetta, GA (US)

(72) Inventors: Kai C. Su, Alpharetta, GA (US); Leslie F. Stebbins, Roswell, GA (US); Bill Mantch, Smyrna, GA (US); Eugene C. Letter, Webster, NY (US)

(73) Assignee: QSPEX TECHNOLOGIES, INC., Alpharetta, GA (US)

( * ) Notice: Subject to any disclaimer, the term of this patent is extended or adjusted under 35 U.S.C. 154(b) by 286 days.

This patent is subject to a terminal disclaimer.

(21) Appl. No.: 13/943,570

(22) Filed: Jul. 16, 2013

(65) Prior Publication Data

US 2013/0301133 A1  Nov. 14, 2013

Related U.S. Application Data

(63) Continuation-in-part of application No. 13/088,199, filed on Apr. 15, 2011, now abandoned, and a continuation-in-part of application No. 13/648,642, filed on Oct. 10, 2012, now Pat. No. 9,042,019.

(51) Int. Cl.
*G02B 1/11* (2015.01)
*B82Y 20/00* (2011.01)
(Continued)

(52) U.S. Cl.
CPC .. *G02B 1/11* (2013.01); *B05D 5/06* (2013.01); *B82Y 20/00* (2013.01); *B82Y 30/00* (2013.01); *B82Y 40/00* (2013.01); *C07F 7/1868* (2013.01); *G02B 1/115* (2013.01)

(58) Field of Classification Search
CPC ............ G02B 1/10; G02B 1/11; G02B 1/111; G02B 1/113; G02B 1/115; G02B 1/18; B05D 5/06; B82Y 30/00; B82Y 40/00; B82Y 20/00; C07F 7/1868

See application file for complete search history.

(56) References Cited

U.S. PATENT DOCUMENTS

| 4,615,947 A | 10/1986 | Goossens |
| 5,025,049 A | 6/1991 | Takarada et al. |

(Continued)

FOREIGN PATENT DOCUMENTS

| CN | 101724342 A | 6/2010 |
| JP | 2007-504500 A | 3/2007 |

OTHER PUBLICATIONS

Korean Intellectual Property Office (ISR/KR), "International Search Report and Written Opinion", PCT/US2014/038600, Korea, Sep. 26, 2014.

(Continued)

*Primary Examiner* — Kimberly N Kakalec
(74) *Attorney, Agent, or Firm* — Tim Tingkang Xia, Esq.; Locke Lord LLP

(57) ABSTRACT

The present invention relates to a method of applying an anti-reflective coating to an optical surface of a mold. In one embodiment, the method includes the steps of providing a lens mold having an optical surface; forming a layer of a super hydrophobic material over the optical surface, wherein the super hydrophobic material contains an amount of dipodal silane that is a relative percentage of the super hydrophobic material; forming an anti-reflective coating layered structure over the layer of the super hydrophobic material; and forming a layer of a coupling agent deposited with a monolayer thickness to the anti-reflective coating layered structure using vapor deposition under aprotic conditions or by dip coating or spin coating using a solution of a coupling agent in an aprotic solvent.

34 Claims, 5 Drawing Sheets

(51) Int. Cl.

| | | |
|---|---|---|
| *C07F 7/18* | (2006.01) | |
| *B82Y 30/00* | (2011.01) | |
| *G02B 1/115* | (2015.01) | |
| *B82Y 40/00* | (2011.01) | |
| *B05D 5/06* | (2006.01) | |

(56) References Cited

U.S. PATENT DOCUMENTS

| | | | |
|---|---|---|---|
| 5,096,626 | A | 3/1992 | Takamizawa et al. |
| 5,621,017 | A | 4/1997 | Kobayakawa et al. |
| 5,733,483 | A | 3/1998 | Soane et al. |
| 5,763,511 | A | 6/1998 | Chan et al. |
| 5,981,634 | A | 11/1999 | Smith et al. |
| 6,017,121 | A | 1/2000 | Chateau et al. |
| 6,114,437 | A | 9/2000 | Brown et al. |
| 6,150,430 | A | 11/2000 | Walters et al. |
| 6,162,844 | A | 12/2000 | Lally et al. |
| 6,171,525 | B1 | 1/2001 | Effer et al. |
| 6,177,507 | B1 | 1/2001 | Calderada |
| 6,250,758 | B1 | 6/2001 | Yoshihara et al. |
| 6,328,446 | B1 | 12/2001 | Bhalakia et al. |
| 6,368,523 | B1 | 4/2002 | Buazza et al. |
| 6,486,226 | B2 | 11/2002 | Al-Akhdar et al. |
| 6,506,488 | B1 | 1/2003 | Stewart et al. |
| 6,531,076 | B2 | 3/2003 | Crano et al. |
| 6,634,879 | B2 | 10/2003 | Buazza et al. |
| 6,712,596 | B1 | 3/2004 | Buazza et al. |
| 6,773,108 | B2 | 8/2004 | deRojas et al. |
| 6,777,459 | B2 | 8/2004 | Al-Akhdar et al. |
| 6,780,546 | B2 | 8/2004 | Trentler et al. |
| 6,786,598 | B2 | 9/2004 | Buazza |
| 6,811,727 | B2 | 11/2004 | Havens et al. |
| 6,863,844 | B2 | 3/2005 | Engardio et al. |
| 6,939,899 | B2 | 9/2005 | Buazza et al. |
| 6,986,857 | B2 | 1/2006 | Klemm et al. |
| 7,087,698 | B1 | 8/2006 | Okoroafor et al. |
| 7,098,290 | B1 | 8/2006 | Okoroafor et al. |
| 7,169,941 | B2 | 1/2007 | Nagoh et al. |
| 7,189,456 | B2 | 3/2007 | King |
| 7,247,262 | B2 | 7/2007 | Evans et al. |
| 7,261,843 | B2 | 8/2007 | Knox et al. |
| 7,335,702 | B2 | 2/2008 | La Dous |
| 7,410,691 | B2 | 8/2008 | Blackburn et al. |
| 7,439,278 | B2 | 10/2008 | Jallouli |
| 7,452,611 | B2 | 11/2008 | Blackburn et al. |
| 7,465,414 | B2 | 12/2008 | Knox et al. |
| 7,666,331 | B2 | 2/2010 | King et al. |
| 7,767,728 | B2 | 8/2010 | Lu et al. |
| 7,811,480 | B2 | 10/2010 | King |
| 7,854,863 | B2 | 12/2010 | Drotleff et al. |
| 7,884,992 | B1 | 2/2011 | Wang et al. |
| 7,961,372 | B2 | 6/2011 | Kim et al. |
| 8,133,274 | B2 | 3/2012 | Zhou et al. |
| 8,137,595 | B2 | 3/2012 | Kim et al. |
| 8,298,671 | B2 | 10/2012 | Qin et al. |
| 8,323,535 | B2 | 12/2012 | Choi et al. |
| 8,367,211 | B2 | 2/2013 | Qin et al. |
| 8,608,988 | B2 | 12/2013 | Bowles et al. |
| 9,042,019 | B2 * | 5/2015 | Su .................... G02B 1/115 359/581 |
| 2003/0122269 | A1 | 7/2003 | Weber et al. |
| 2003/0129397 | A1 | 7/2003 | Wilson et al. |
| 2004/0065968 | A1 | 4/2004 | Klemm et al. |
| 2005/0233070 | A1 | 10/2005 | Pellerite et al. |
| 2006/0012889 | A1 | 1/2006 | Kojima et al. |
| 2006/0079388 | A1 | 4/2006 | Koenig et al. |
| 2006/0176571 | A1 | 8/2006 | Mosse et al. |
| 2007/0173582 | A1 | 7/2007 | Rukavina et al. |
| 2008/0058444 | A1 | 3/2008 | Tanaka et al. |
| 2008/0113188 | A1 | 5/2008 | Shah et al. |
| 2008/0146816 | A1 | 6/2008 | Fabre-Francke et al. |
| 2009/0075092 | A1 | 3/2009 | Varaprasad |
| 2009/0093601 | A1 | 4/2009 | Evans et al. |
| 2010/0104838 | A1 * | 4/2010 | Noguchi ............. G02B 1/115 428/212 |
| 2011/0147681 | A1 | 6/2011 | Evans et al. |
| 2012/0107581 | A1 | 5/2012 | Simpson et al. |
| 2013/0015416 | A1 | 1/2013 | Takenaka et al. |
| 2013/0242368 | A1 | 9/2013 | Ofir et al. |
| 2013/0273380 | A1 | 10/2013 | Hickenboth et al. |
| 2015/0212237 | A1 * | 7/2015 | Su .................... G02B 1/115 359/581 |

OTHER PUBLICATIONS

Arkles et al., Cyclic azasilanes: volatile coupling agents for nanotechnology, Silanes and Other Coupling Agents, vol. 3, pp. 179-191, 2004.

* cited by examiner

Structure 1. Cyclic Azasilane
N-n-BUTYL-AZA-2,2-DIMETHOXY SILACYCLOPENTANE

+

Structure 2

Ring opening reaction
(no water or heat required)

Structure 3

ANTI-REFLECTIVE LENSES AND METHODS FOR MANUFACTURING THE SAME

CROSS-REFERENCE TO RELATED APPLICATIONS

This application is a continuation-in-part of U.S. patent application Ser. No. 13/088,199, filed Apr. 15, 2011, entitled "ANTI-REFLECTIVE LENSES AND METHODS FOR MANUFACTURING THE SAME" by Kai C. Su, Leslie F. Stebbins, Bill Mantch, and Eugene C. Letter. The disclosure of the above identified co-pending application is incorporated herein by reference in its entirety.

This application is also a continuation-in-part of U.S. patent application Ser. No. 13/648,642, filed Oct. 10, 2012, entitled "ANTI-REFLECTIVE LENSES AND METHODS FOR MANUFACTURING THE SAME" by Kai C. Su, Leslie F. Stebbins, Bill Mantch, and Eugene C. Letter. The disclosure of the above identified co-pending application is incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference were individually incorporated by reference.

FIELD OF THE INVENTION

The present invention relates generally to an optical surface, and more particularly to an anti-reflective lens and methods of manufacturing the same.

BACKGROUND OF THE INVENTION

An anti-reflective lens normally is formed with an anti-reflective coating on a plastic ophthalmic lens. Anti-reflective (AR) coatings are applied to the surfaces of ophthalmic lenses and other optical devices to reduce reflection. For ophthalmic lenses in particular, the reduced reflection makes them not only look better, but more importantly work better because they produce less glare by eliminating multiple reflections, which is particularly noticeable when driving at night or working in front of a computer monitor. The decreased glare means that wearers often find their eyes are less tired, particularly at the end of the day. AR coatings also allow more light to pass through the lens, which increases contrast and therefore increases visual acuity.

The art of casting plastic ophthalmic lenses involves introducing a lens-forming material between two molds and then polymerizing the lens-forming material to become a solid. Liquid plastic formulations such as CR39 monomer are injected into a cavity formed by front and rear molds which have been provided with interior polished mold surfaces for the finished surfaces of the lenses. The plastic is cured in the mold, and then the mold is separated to yield a completed ophthalmic lens which meets a selected prescription. The lens is then ground around the edge to fit into the selected frame. Coatings can be applied to the finished lens or to the inside of the front or rear mold, whereupon they will bond to the lens upon curing.

Some optometrists offer on-site eyeglass services. Several companies have developed methods by which lenses can be cast on site, in an office. However, current methods of applying AR coatings to eyeglasses require that they be shipped to a different facility because the AR coatings must be applied via vacuum vapor deposition. This of course means additional time and expense. There is therefore a need for a method for making eyeglasses with an AR coating on-site.

One type of AR coating that is used for ophthalmic lenses is an alternating stack of a high index material and a low index material. The most commonly used low index material is silicon dioxide; zirconium dioxide and/or titanium dioxide is often used as the high index material.

An issue with AR coatings, particularly as applied to plastic ophthalmic lenses, is adhesion. AR coatings are generally applied via vacuum deposition. It is well known that adhesion of vacuum-deposited coatings to their substrates is in general problematic. The organic, plastic lens material and inorganic AR material do not readily adhere to each other, resulting in peeling or scratching. Accordingly, a new method is needed to apply an AR coating to a plastic lens with greater adhesion.

Several patents are understood to disclose using silanes to bind an inorganic matrix to an organic matrix. U.S. Pat. No. 5,733,483 to Soane et al. teaches using a coupling layer to tie together an AR multilayer made of silicon oxide and an acrylate-containing lens. The coupling agent has a siloxy head and an acrylate tail. An example of a silane used therein is methacryloxypropyltrimethoxysilane.

U.S. Pat. No. 4,615,947 to (loosens teaches an acrylic mixed with an organopolysiloxane to increase the adhesion of an organosiloxane hard coat to a thermoplastic substrate. U.S. Pat. No. 5,025,049 to Takarada et al. also teaches a primer for increasing adhesion of an organopolysiloxane layer to a thermoplastic substrate. The primer is a mixture of an organic copolymer including an alkoxysilylated monomer and other ingredients.

Other patents discuss using silanes to bind an organic matrix to another organic matrix. U.S. Pat. No. 6,150,430 to Walters et al. teaches using organofunctional silanes to improve the adherence of an organic polymeric layer to an organic polymeric substrate.

U.S. Pat. No. 5,096,626 to Takamizawa et al. teaches a plastic lens having an AR coating and/or hard coat. The patent discusses poor adhesion of prior art methods and says they achieve excellent adhesion by forming the lens using a set of molds, wherein the AR coating is first applied to one of the molds and then the lens monomer is poured between the molds and polymerized. A silane coupling agent such as methacryloxypropyltrimethoxysilane can be included in the hard coat/AR coat solution, which may contain colloidal silica, colloidal antimony oxide or colloidal titanium dioxide.

U.S. Pat. No. 6,986,857 to Klemm et al. teaches a method of assembling a lens with a top coat, AR coat, scratch resistant coat, impact resistant primer, and lens substrate. Klemm's solution to the issue of poor adherence of the top coat to the AR coat is to apply the first layer of the AR coating (which comprises a stack of four layers) as two sublayers of $SiO_2$. Another thin layer of $SiO_2$ is applied between the AR stack and the scratch resistant coating to improve adherence between the two.

The above references in general use sol gel chemistry and require high heat ($\geq 80°$ C.). Heating to high temperature, however, is not suitable for casting and curing lenses in plastic molds because the optical surface of the mold will be distorted.

Therefore, a heretofore unaddressed need exists in the art to address the aforementioned deficiencies and inadequacies.

SUMMARY OF THE INVENTION

In one aspect, the present invention relates to a method of applying an anti-reflective (AR) coating to a plastic substrate such as a plastic ophthalmic lens where the AR coating exhibits good adhesion to the substrate, where the method eliminates both an initial $SiO_2$ or $MgF_2$ layer and a mold release layer. The super hydrophobic can now be applied directly to the mold surface.

In one embodiment, the method includes the steps of providing a lens mold having an optical surface; forming a layer of a super hydrophobic material over the optical surface, by heating a thermal boat that is in contact with one or more crucibles containing the super hydrophobic material to a temperature between about 200° C. and about 500° C., wherein the super hydrophobic material contains an amount of dipodal silane that is a relative percentage of the super hydrophobic material; forming an AR coating layered structure over the layer of the super hydrophobic material; and forming a layer of a coupling agent deposited with a monolayer thickness to the AR coating layered structure using vapor deposition under aprotic conditions or by dip coating or spin coating using a solution of a coupling agent in an aprotic solvent. In one embodiment, the thermal boat is heated by a low voltage high amperage current. In another embodiment, the thermal boat is heated by an electron beam. In other embodiments, a combination of heating methods is used. In some embodiments, the crucible in contact with the thermal boat contains ceramic or metal pills in which the super hydrophobic material is adsorbed.

In one embodiment, the amount of the dipodal silane is about 1.7-8.3% of the super hydrophobic material by weight.

In one embodiment, the dipodal silane comprises bis(trimethoxysilylpropyl)amine.

In one embodiment, the layer of the coupling agent is formed of a composition that comprises cyclic azasilanes, wherein the layer of the coupling agent is formed of N-n-butyl-aza-2,2-dimethoxy-silacyclopentane. In another embodiment, the layer of the coupling agent is formed of a composition comprising dipodal silane.

In one embodiment, the step of forming the AR coating layered structure over the layer further comprises the steps of forming a first layer of a first material with a first index of refraction and a thickness of about 5 to 100 nm, on the layer of the super hydrophobic material; forming a second layer of a second material with a second index of refraction that is higher than the first index of refraction and a thickness of about 40 to 50 nm, on the first layer; forming a third layer of the first material with the first index of refraction and a thickness of about 10 to 20 nm, on the second layer; forming a fourth layer of the second material with the second index of refraction and a thickness of about 50 to 70 nm, on the third layer; forming a fifth layer of the first material with the first index of refraction and a thickness of about 25 to 40 nm, on the fourth layer; forming a sixth layer of the second material with the second index of refraction and a thickness of about 10 to 25 nm, on the fifth layer; and forming a seventh layer of the first material with the first index of refraction and a thickness of about 5 to 15 nm, on the sixth layer, where the first material with the first index of refraction is $SiO_2$, and the second material with the second index of refraction is $ZrO_2$. In one embodiment, each layer of $SiO_2$ is deposited using ion assist or without using ion assist.

In one embodiment, the method further includes the step of forming a layer of $SiO_2$ between the AR coating layered structure and the layer of the super hydrophobic material.

In another aspect, the present invention relates to a mold with an optical surface having an AR coating that is transferable to a lens. In one embodiment, the mold has a layer of a super hydrophobic material formed over the optical surface, by heating a thermal boat that is in contact with one or more crucibles containing the super hydrophobic material to a temperature between about 200° C. and about 500° C., wherein the super hydrophobic material contains an amount of dipodal silane that is a relative percentage of the super hydrophobic material; an AR coating layered structure formed over the layer of the super hydrophobic material; and a layer of a coupling agent deposited with a monolayer thickness to the anti-reflective coating layered structure using vapor deposition under aprotic conditions or by dip coating or spin coating using a solution of a coupling agent in an aprotic solvent.

In one embodiment, the mold further includes a layer of $SiO_2$ formed between the AR coating layered structure and the layer of the super hydrophobic material.

In one embodiment, the amount of the dipodal silane is about 1.7-8.3% of the super hydrophobic material by weight.

In one embodiment, the AR coating layered structure comprises a first layer of a first material with a first index of refraction and a thickness of about 5 to 100 nm, formed on the layer of the super hydrophobic material; a second layer of a second material with a second index of refraction that is higher than the first index of refraction and a thickness of about 40 to 50 nm, formed on the first layer; a third layer of the first material with the first index of refraction and a thickness of about 10 to 20 nm, formed on the second layer; a fourth layer of the second material with the second index of refraction and a thickness of about 50 to 70 nm, formed on the third layer; a fifth layer of the first material with the first index of refraction and a thickness of about 25 to 40 nm, formed on the fourth layer; a sixth layer of the second material with the second index of refraction and a thickness of about 10 to 25 nm, formed on the fifth layer; and a seventh layer of the first material with the first index of refraction and a thickness of about 5 to 15 nm, formed on the sixth layer. In one embodiment, the first material with the first index of refraction is $SiO_2$, and the second material with the second index of refraction is $ZrO_2$. In one embodiment, each layer of $SiO_2$ is deposited using ion assist or without using ion assist.

In one embodiment, the dipodal silane comprises bis(trimethoxysilylpropyl)amine.

In one embodiment, the layer of the coupling agent is formed of a composition that comprises cyclic azasilanes. In one embodiment, the layer of the coupling agent is formed of N-n-butyl-aza-2,2-dimethoxy-silacyclopentane.

In yet another aspect, the present invention relates to an optical lens manufactured with a mold having an optical surface. In one embodiment, the optical lens has a lens body with an optical surface; a hard coat layer over the optical surface of the lens body; and an AR coating. The AR coating includes a layer of a super hydrophobic material formed over the optical surface of the mold, by heating a thermal boat that is in contact with one or more crucibles containing the super hydrophobic material to a temperature between about 200° C. and about 500° C., wherein the super hydrophobic material contains an amount of dipodal silane that is a relative percentage of the super hydrophobic material; an anti-reflective coating layered structure formed over the layer of the super hydrophobic material; and a layer of a coupling agent deposited with a monolayer thickness to the anti-reflective coating layered structure. The hard coat layer is substantially in contact with the layer of the coupling agent of the anti-reflective coating.

In one embodiment, the AR coating layered structure comprises a first layer of a first material with a first index of refraction and a thickness of about 5 to 100 nm, formed on the layer of the super hydrophobic material; a second layer of a second material with a second index of refraction that is higher than the first index of refraction and a thickness of about 40 to 50 nm, formed on the first layer; a third layer of the first material with the first index of refraction and a thickness of about 10 to 20 nm, formed on the second layer; a fourth layer of the second material with the second index of refraction and a thickness of about 50 to 70 nm, formed on the third layer; a fifth layer of the first material with the first index of refraction and a thickness of about 25 to 40 nm, formed on the fourth layer; a sixth layer of the second material with the second index of refraction and a thickness of about 10 to 25 nm, formed on the fifth layer; and a seventh layer of the first material with the first index of refraction and a thickness of about 5 to 15 nm, formed on the sixth layer. In one embodiment, the first material with the first index of refraction is $SiO_2$, and the second material with the second index of refraction is $ZrO_2$. In one embodiment, each layer of $SiO_2$ is deposited using ion assist or without using ion assist.

In one embodiment, the amount of the dipodal silane is about 1.7-8.3% of the super hydrophobic material by weight.

In one embodiment, the dipodal silane comprises bis(trimethoxysilylpropyl)amine.

In one embodiment, the layer of the coupling agent is formed of a composition that comprises cyclic azasilanes. In one embodiment, the layer of the coupling agent is formed of N-n-butyl-aza-2,2-dimethoxy-silacyclopentane.

In one embodiment, the optical lens further comprises a layer of $SiO_2$ formed between the AR coating layered structure and the layer of the super hydrophobic material.

In a further aspect, the present invention relates to a method for applying an AR coating to an optical surface of a mold. In one embodiment, the method includes the steps of providing a lens mold having an optical surface; forming a layer of a super hydrophobic material over the optical surface, wherein the super hydrophobic material contains an amount of dipodal silane that is a relative percentage of the super hydrophobic material; forming an AR coating layered structure over the layer of the super hydrophobic material; and forming a layer of a coupling agent deposited with a monolayer thickness to the AR coating layered structure using vapor deposition under aprotic conditions or by dip coating or spin coating using a solution of a coupling agent in an aprotic solvent. In one embodiment, the amount of the dipodal silane is about 1.7-8.3% of the super hydrophobic material by weight.

In one embodiment, the step of forming an AR coating layered structure over the layer further comprises the steps of forming a first layer of a first material with a first index of refraction on the layer of the super hydrophobic material; forming a second layer of a second material with a second index of refraction on the first layer; forming a third layer of the first material with the first index of refraction on the second layer; forming a fourth layer of the second material with the second index of refraction on the third layer; forming a fifth layer of the first material with the first index of refraction on the fourth layer; forming a sixth layer of the second material with the second index of refraction on the fifth layer; and forming a seventh layer of the first material with the first index of refraction on the sixth layer. In one embodiment, the first index of refraction and the second index of refraction satisfy a ratio of H/L>1, where L and H are values of the first and second index of refraction, respectively. In one embodiment, the first material with the first index of refraction is $SiO_2$, and the second material with the second index of refraction is $ZrO_2$.

In one embodiment, the layer of coupling agent is formed of a composition that comprises cyclic azasilanes.

In one embodiment, the step of forming the layer of super hydrophobic material over the optical surface comprises heating a thermal boat that is in contact with one or more crucibles containing the super hydrophobic material. In one embodiment, the heating step comprises heating the thermal boat to a temperature between about 200° C. and about 500° C.

In yet a further aspect, the present invention relates to a mold with an optical surface having an AR coating that is transferable to a lens. In one embodiment, the mold has a layer of a super hydrophobic material formed over the optical surface, wherein the super hydrophobic material contains an amount of dipodal silane that is a relative percentage of the super hydrophobic material; an AR coating layered structure formed over the layer of the super hydrophobic material; and a layer of a coupling agent deposited with a monolayer thickness to the AR coating layered structure using vapor deposition under aprotic conditions or by dip coating or spin coating using a solution of a coupling agent in an aprotic solvent. In one embodiment, the amount of the dipodal silane is about 1.7-8.3% of the super hydrophobic material by weight.

In one embodiment, the layer of super hydrophobic material is formed over the optical surface by heating a thermal boat that is in contact with one or more crucibles containing the super hydrophobic material, at a temperature, wherein the temperature is between about 200° C. and about 500° C.

In one embodiment, the AR coating layered structure comprises a first layer of a first material with a first index of refraction formed on the layer of the super hydrophobic material; a second layer of a second material with a second index of refraction formed on the first layer; a third layer of the first material with the first index of refraction formed on the second layer; a fourth layer of the second material with the second index of refraction formed on the third layer; a fifth layer of the first material with the first index of refraction formed on the fourth layer; a sixth layer of the second material with the second index of refraction formed on the fifth layer; and a seventh layer of the first material with the first index of refraction formed on the sixth layer. In one embodiment, the first index of refraction and the second index of refraction satisfy a ratio of H/L>1, where L and H are values of the first and second index of refraction, respectively. In one embodiment, the first material with the first index of refraction is $SiO_2$, and the second material with the second index of refraction is $ZrO_2$.

In one embodiment, the layer of coupling agent is formed of a composition that comprises cyclic azasilanes.

In one aspect, the present invention relates to an optical lens manufactured with a mold having an optical surface. In one embodiment, the optical lens has a lens body with an optical surface; a hard coat layer over the optical surface of the lens body; and an AR coating. The AR coating includes a layer of a super hydrophobic material formed over the optical surface of the mold, wherein the super hydrophobic material contains an amount of dipodal silane that is a relative percentage of the super hydrophobic material; an anti-reflective coating layered structure formed over the layer of the super hydrophobic material; and a layer of a coupling agent deposited with a monolayer thickness to the anti-reflective coating layered structure. The hard coat layer is substantially in contact with the layer of the coupling agent of the anti-reflective coating.

In one embodiment, the layer of the super hydrophobic material is formed over the optical surface of the lens mold by heating a thermal boat that is in contact with one or more crucibles containing the super hydrophobic material, at a temperature. In one embodiment, the temperature is between about 200° C. and about 500° C.

In one embodiment, the amount of the dipodal silane is about 1.7-8.3% of the super hydrophobic material by weight.

In one embodiment, the AR coating layered structure comprises a first layer of a first material with a first index of refraction formed on the layer of the super hydrophobic material; a second layer of a second material with a second index of refraction formed on the first layer; a third layer of the first material with the first index of refraction formed on the second layer; a fourth layer of the second material with the second index of refraction formed on the third layer; a fifth layer of the first material with the first index of refraction formed on the fourth layer; a sixth layer of the second material with the second index of refraction formed on the fifth layer; and a seventh layer of the first material with the first index of refraction formed on the sixth layer. In one embodiment, the first index of refraction and the second index of refraction satisfy a ratio of H/L>1, where L and H are values of the first and second index of refraction, respectively. In one embodiment, the first material with the first index of refraction is $SiO_2$, and the second material with the second index of refraction is $ZrO_2$.

In one embodiment, the layer of the coupling agent is formed of a composition that comprises cyclic azasilanes.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE INVENTION

Figure 1:
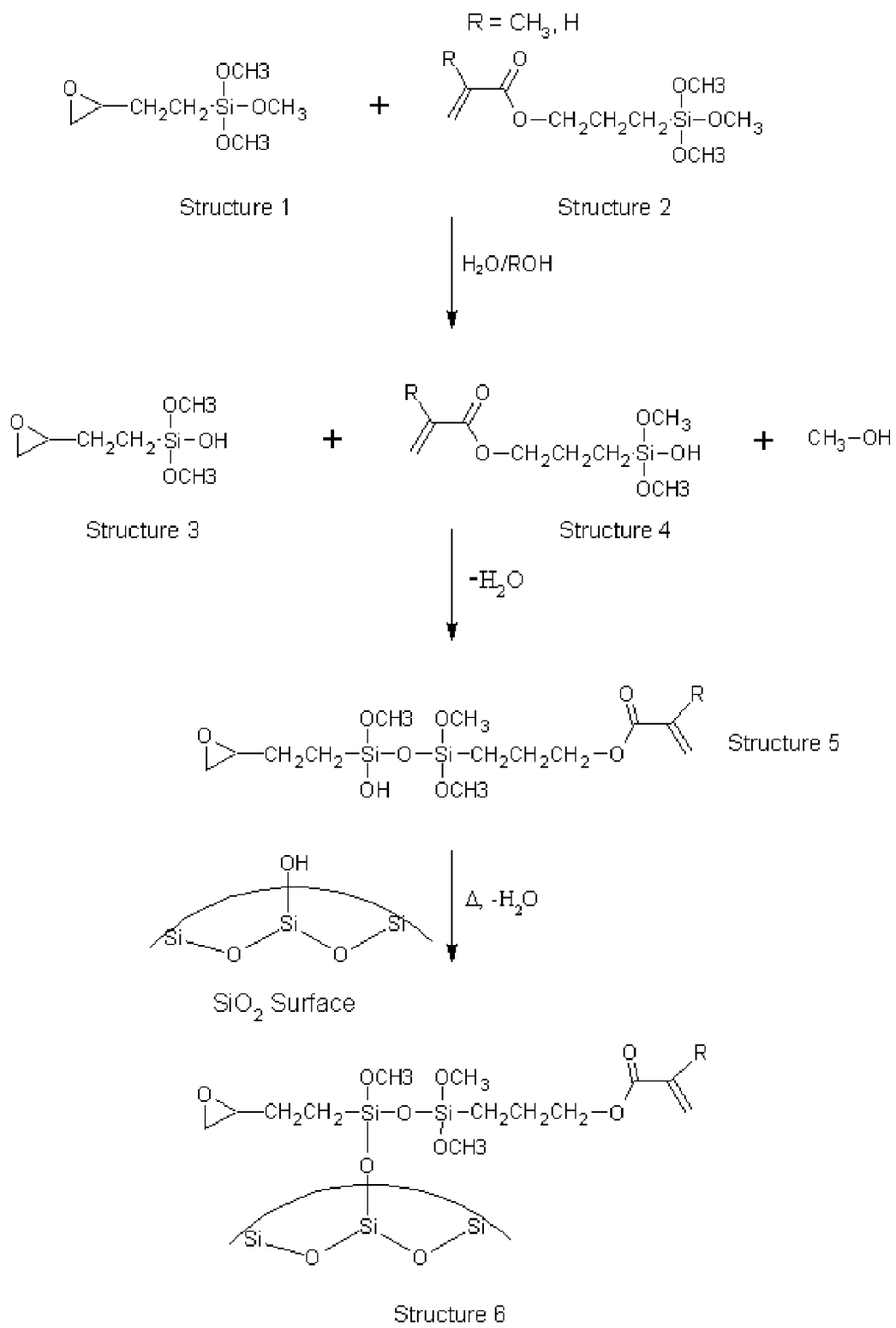
FIG. 1 shows chemical reactions related to coupling agents utilized in prior art for manufacturing an anti-reflective coated lens.

The present disclosure will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom", "upper" or "top", and "left" and "right", may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper", depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

OVERVIEW OF THE INVENTION

The description will be made as to the embodiments of the present invention in conjunction with the accompanying drawings in FIGS. 1-5. In accordance with the purposes of this invention, as embodied and broadly described herein, this invention relates to AR-coated spectacle lenses, molds, compositions and methods of making AR lenses.

The previous procedures outlined in the parent U.S. application Ser. No. 13/088,199, which is incorporated herein by reference in its entirety, require a mold release layer (standard hydrophobic) and a layer of either SiO2 or MgF2 between the hydrophobic material and the mold.

However, according to various embodiments of the present invention, by controlling the temperature at which the super hydrophobic material is applied, both the initial $SiO_2$ or $MgF_2$ layer and the mold release layer can be eliminated. The super hydrophobic material can be applied directly to the mold surface. The super hydrophobic material used in the examples of the specification was, but not limited to, Daikin Optool DSX. It should be appreciated that other super hydrophobic materials can also be utilized to practice the invention.

In one embodiment, the super hydrophobic material is applied at less than 540 degrees C. (as measured on the thermal boat). The preferred temperature range is about 250-500 degrees C.

The super hydrophobic layer may be anywhere from 20 nm to 100 nm thick, with a preferred thickness of 40 nm.

According to embodiments of the present invention, dipodal is still required to stabilize the super hydrophobic layer. The dipodal is placed into the pill along with the super hydrophobic, and they are applied together. In one embodiment, in a Satis 1200 chamber, the amount of dipodal mixed with the super hydrophobic must be between 0.01 g and 0.1 g per pill. Two pills are used in a single run. The preferred weight of the dipodal (for a 40 nm super hydrophobic layer) is 0.04 g per pill.

Dipodal silanes are available from Gelest, Inc. A preferred dipodal silane can be bis(trimethoxysilylpropyl)amine having the formula:

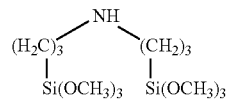

In one embodiment, the super hydrophobic material contains about 1.7-8.3% of dipodal silane by weight relative to the super hydrophobic material.

The super hydrophobic layer on the mold is not a mold release layer. The super hydrophobic layer transfers to, and becomes part of, the lens during lens casting and curing.

Subsequent to the super hydrophobic coating, an anti-reflective (AR) coating is applied. The AR coating is a layered structure with multiple layers of dielectric materials (4 to 7 layers or even more) that are applied by vacuum deposition such that the last layer is ion-assisted $SiO_2$. Preferably, the AR coating is a layered structure with multiple layers of three or more dielectric materials having alternating high and low refractive indexes.

A layer of silane coupling agent is applied to the AR-coated mold to promote adhesion of the hard coating. The coupling agent layer must be applied under aprotic conditions. This can be done using methods commonly practiced in the lens industry today (such as spin, spray, dip, vacuum coating). The coupling agent layer is applied at room temperature. The silane coupling agent may be a dipodal silane. Alternatively, the silane coupling agent is a cyclic azasilane. The silane from the cyclic azasilane will bond to the AR coating and the functional group will bond with the organic hard coat, respectively.

The next coating layer applied to the mold is the scratch-resistant (hard) coating. The hard coat can be applied by conventional methods used in the lens industry, including spin, spray, or dip coating followed by curing.

The exemplary process illustrated above can be repeatedly applied to different optical surfaces of an optical mold assembly containing a front mold and a back mold. Following the applications of the coating to both of the front and back molds, the molds are assembled with a spacer ring to form the optical mold assembly. The cavity of the assembly is then filled with lens material formulation and cured. After the cure is complete, the lens is removed from the assembly. All coatings are transferred to the lens so that the lens has super hydrophobic, anti-reflective, and scratch resistance coatings applied. This process may also be used to make polarized and photochromic lenses.

Thus, in one aspect, more specifically, the invention relates to a method for making an AR-coated plastic substrate having good adhesion of the AR coating. The plastic substrate in one embodiment is a plastic ophthalmic spectacle lens.

In another aspect, the invention relates to a method of making AR coated plastic ophthalmic spectacle lenses on-site.

An AR coating is commonly applied to the surface of lenses to reduce reflection. Often, the AR coating is made of multiple layers of high index and low index materials such as $ZrO_2$ and $SiO_2$. One problem with inorganic silica AR coatings is that they do not readily adhere to plastic organic lenses. The present invention successfully solves the problem by, among other things, using a coupling layer between the inorganic silica AR coating and the lens. In one embodiment of the present invention, the coupling layer is formed by utilizing cyclic azasilane. In another embodiment, the coupling layer is formed by utilizing a dipodal silane.

In general, the method for forming an ophthalmic lens having an AR coating thereon is comprised of the steps of preparing first and second molds having optical surfaces facing each other. In a preferred embodiment, molds and a gasket such as described in U.S. Pat. No. 7,114,696, which is incorporated herein by reference in its entirety, are used. Various desired coatings are applied to the interior of one or both molds. The molds with the coatings thereon are placed in a gasket assembly which provides a space between the molds. A liquid monomer is placed in the space and is cured to provide a lens.

The molds can be formed of any suitable material which is capable of withstanding the processing temperatures hereinafter utilized and which can provide surfaces of the type required for the optical elements being prepared.

In one embodiment of the present invention, as a first step, a coating is applied by electron beam deposition directly onto the plastic mold optical surface. Subsequent to the first coating, a second coating may be applied before a multilayer AR coating is applied in reverse order. In one embodiment of the present invention, an AR coating is a multilayer structure with alternating layers formed with two different materials, a high index material and a low index material. In one preferred embodiment of the present invention, an AR coating is a multilayer structure with 7 alternating layers formed with two different materials, a high index material and a low index material with a ratio H/L>1, wherein L and H are values of the first and second index of refraction, respectively. Materials found to be suitable for practicing the present invention are zirconium dioxide (referred as "$ZrO_2$") as a high index material and silicon dioxide as a low index material, having an index of refraction of approximately 1.46.

In one embodiment of the present invention, the layers are applied by vacuum deposition such that the first and last layers are silicon dioxide ($SiO_2$).

Following the AR coating application, a layer or film of the coupling agent is applied by vapor phase deposition. When the coupling agent is cyclic azasilane, it will bond to surface hydroxyls on the silicon dioxide layer, opening the ring and resulting in an organic molecule on the surface. This can be done under vacuum, at room temperature, and does not require water as a catalyst.

Next, a scratch resistant (hard) coating is applied. The hard coat can be applied as either an extension of the AR coating process by vacuum deposition or by the more conventional methods of spin, spray, or dip coating, with the coating application followed by curing.

Following the application of the various coatings to the mold, a front and back mold are assembled. The cavity of the assembly is then filled with lens material formulation which is then cured and bonds to the hard coat. After the cure is complete, the lens is removed from the assembly. All coatings are transferred to the lens so that the lens has super hydrophobic, anti-reflective, and scratch resistance coatings applied.

Cyclic azasilanes are available from Gelest, Inc. Generic formulas include azasilacyclopentanes having the formula:

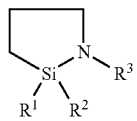

where $R^1$ and $R^2$ are independently selected from the group consisting of branched and linear, substituted and unsubstituted alkyl, alkenyl and alkoxy groups, and where $R^3$ is selected from the group consisting of substituted and unsubstituted, saturated and unsaturated, branched and linear aliphatic hydrocarbon groups; substituted and unsubstituted, branched and linear aralkyl groups; substituted and unsubstituted aryl groups; and hydrogen. Cyclic azasilanes also include diazasilacyclic compounds having the formula:

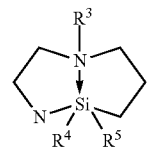

where $R^3$ is selected from the group consisting of substituted and unsubstituted, saturated and unsaturated, branched and linear aliphatic hydrocarbon groups; substituted and unsubstituted, branched and linear aralkyl groups; substituted and unsubstituted aryl groups; and hydrogen; and wherein $R_4$ and $R_5$ are independently selected from the group consisting of substituted and unsubstituted, branched and linear alkyl and alkoxy groups.

A preferred super hydrophobic compound is Optool DSX available from Daikin. This hydrophobic compound does not contain additives that are typically included in commercial super hydrophobic preparations to increase sticking of the super hydrophobic material to a plastic lens.

These and other aspects of the present invention are more specifically described below.

IMPLEMENTATIONS AND EXAMPLES OF THE INVENTION

Without intent to limit the scope of the invention, additional exemplary embodiments and their related results according to the embodiments of the present invention are given below. Note that titles or subtitles may be used in the examples for convenience of a reader, which in no way should limit the scope of the invention. Moreover, certain theories are proposed and disclosed herein; however, in no way should they, whether they are right or wrong, limit the scope of the invention so long as the invention is practiced according to the invention without regard for any particular theory or scheme of action.

Example 1

Cyclic Azasilanes

Various types of cyclic azasilanes can be used to practice the present invention, including:

(a) SIB1932.4 or N-n-BUTYL-AZA-2,2-DIMETHOXYSILACYCLOPENTANE, C9H21NO2Si, with the following formula:

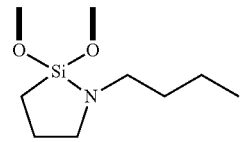

(b) SID3543.0 or 2,2-DIMETHOXY-1,6-DIAZA-2-SILACYCLOOCTANE, C7H18N2O2Si, with the following formula:

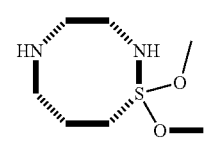

(c) SIA0592.0 or N-AMINOETHYL-AZA-2,2,4-TRIM-ETHYLSILACYCLOPENTANE, C8H21NSi, with the following formula:

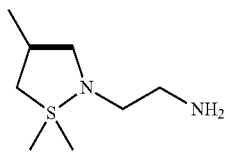

(d) SIA0380.0 or N-ALLYL-AZA-2,2-DIMETHOXYSI-LACYCLOPENTANE C8H17NO2Si, with the following formula:

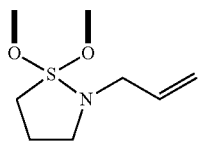

Example 2

Coating Bonding Tests

This example shows various tests utilized for the bonding of coatings produced according to various embodiments of the present invention.

Cross-Hatch Test. In the cross-hatch test, a series of 10 lines spaced 1 mm apart is cut into the coating with a razor blade. A second series of 10 lines spaced 1 mm apart at right angles to and overlaying the first is cut into the coating. A piece of cellophane tape is then applied over the crosshatch pattern and pulled quickly away from the coating.

Crazing Test. In the crazing test, a lens is de-molded then annealed at 80° C. for 20 minutes. The lens is quickly transferred to room temperature water and it is checked for crazing. If no crazing is apparent, then the AR/coupling agent system is acceptable.

Boiling Salt Water Test. In the boiling salt water test, the lens is first immersed for two minutes in a boiling salt solution containing 4.5% NaCl and 0.8% $NaH_2PO_4.2H_2O$. Next, the lens is quickly transferred to room temperature (18-24° C.) deionized water. If no crazing or delamination in the coating is noted, then the AR/coupling agent system is acceptable.

Example 3

Preparation and Application of a Super Hydrophobic Layer

In this Example, among other things, a process of preparation of a super hydrophobic layer is provided according to different embodiments of the present invention.

Using a steel thermal boat, a layer of a super hydrophobic material with a thickness of about 40 nm was deposited onto the molds. The super hydrophobic material was evaporated from two copper crucibles, also called copper "liners", containing steel wool, each of which contained 0.04 g dipodal silane and excess super hydrophobic. As shown in the following examples, the quality of the AR coating and the resulting lens are substantially dependent on the temperature of the steel thermal boat at which the super hydrophobic layer was applied. All temperature measurements were taken by recording the temperature of the steel thermal boat during deposition.

Example (A): The temperature of the steel boat was raised to 1350 degrees Fahrenheit (approximately 730 degrees Celsius). As a result, thin vein-like marks were visible in the AR coating. Crazing occurred on the resulting lenses.

Example (B): The temperature of the steel boat was raised to 1200 degrees Fahrenheit (approximately 650 degrees Celsius). No vein-like marks were visible, but crazing occurred on the resulting lenses. Furthermore, the lenses failed a contact angle test.

Example (C): The temperature of the steel boat was raised to 1000 degrees Fahrenheit (approximately 540 degrees Celsius). Crazing still occurred on the lenses, and the lenses failed a contact-angle test.

Example (D): The temperature of the steel boat was raised to 900 degrees Fahrenheit (approximately 480 degrees Celsius). The lenses did not craze, and contact angle was improved.

Example (E): The temperature of the steel boat was raised to 700 degrees Fahrenheit (approximately 370 degrees Celsius). The lenses did not craze, and contact angle was good.

Example (F): The temperature of the steel boat was raised to 500 degrees Fahrenheit (approximately 260 degrees Celsius). The contact angle was acceptable but not as good as the results in Example 5. It also became more difficult to separate the mold from the lens after casting. No crazing occurred.

Example (G): When the temperature of the boat was raised to 400 degrees Fahrenheit (about 200 degrees Celsius), the coating machine was unable to consistently detect growth of the super hydrophobic layer on the molds.

Figure 3:
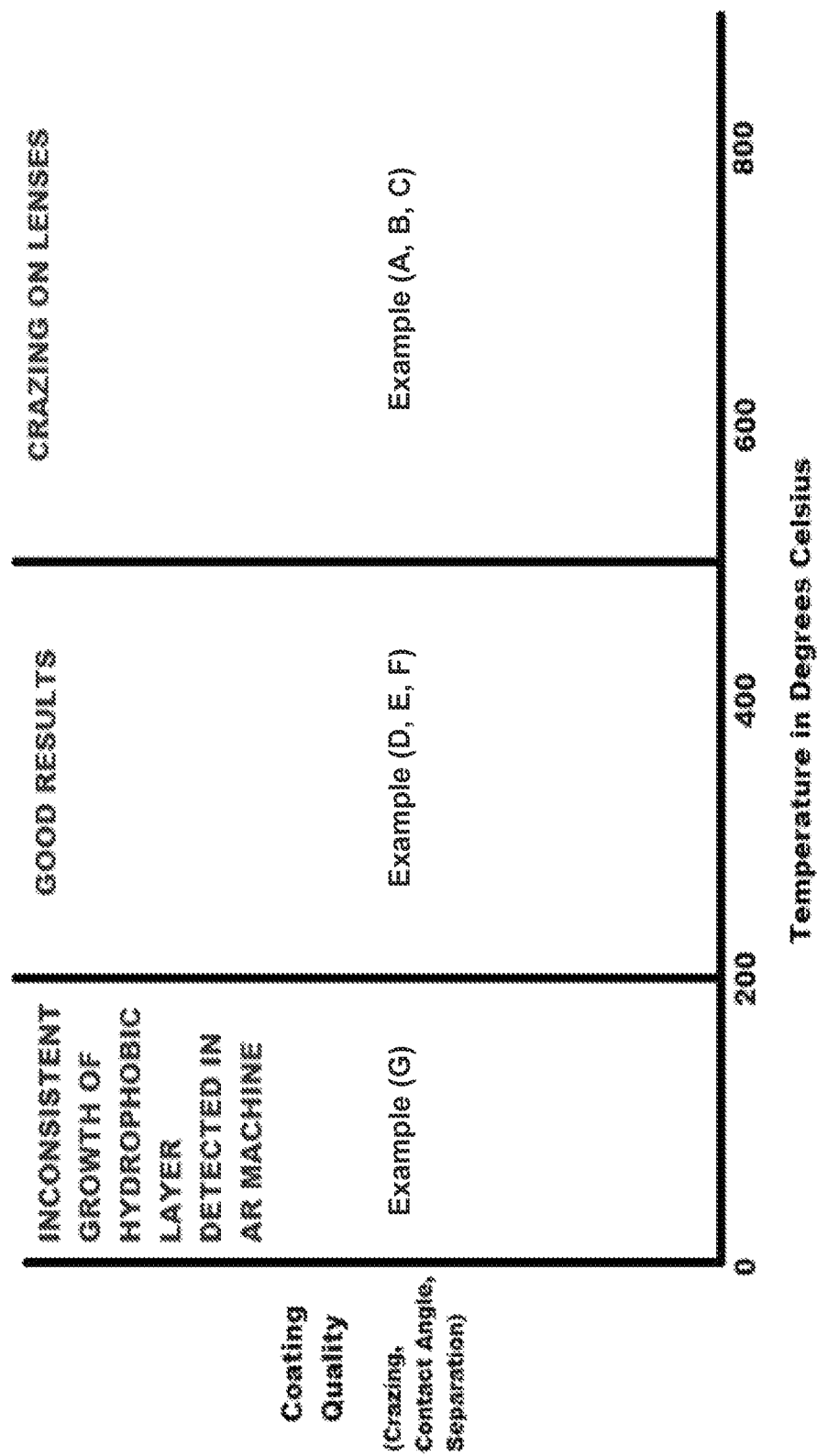
FIG. 3 shows the dependency of the AR coating and the resulting lens on the temperature at which the super hydrophobic layer is applied according to embodiments of the present invention.

FIG. 3 shows the dependency of the AR coating and the resulting lens on the temperature of the steel thermal boat at which the super hydrophobic layer was applied. According to the invention, the preferred temperature range is about 200-500 degrees Celsius.

Example 4

Preparation of an AR Coating that is Applied to a Disposable Mold

In this Example, among other things, a process of preparation of applying an AR coating to a disposable mold is provided according to yet another embodiment of the present invention. It is noted that in this Example, $SiO_2$ layers are formed or deposited with or without ion assist.

Figure 4:
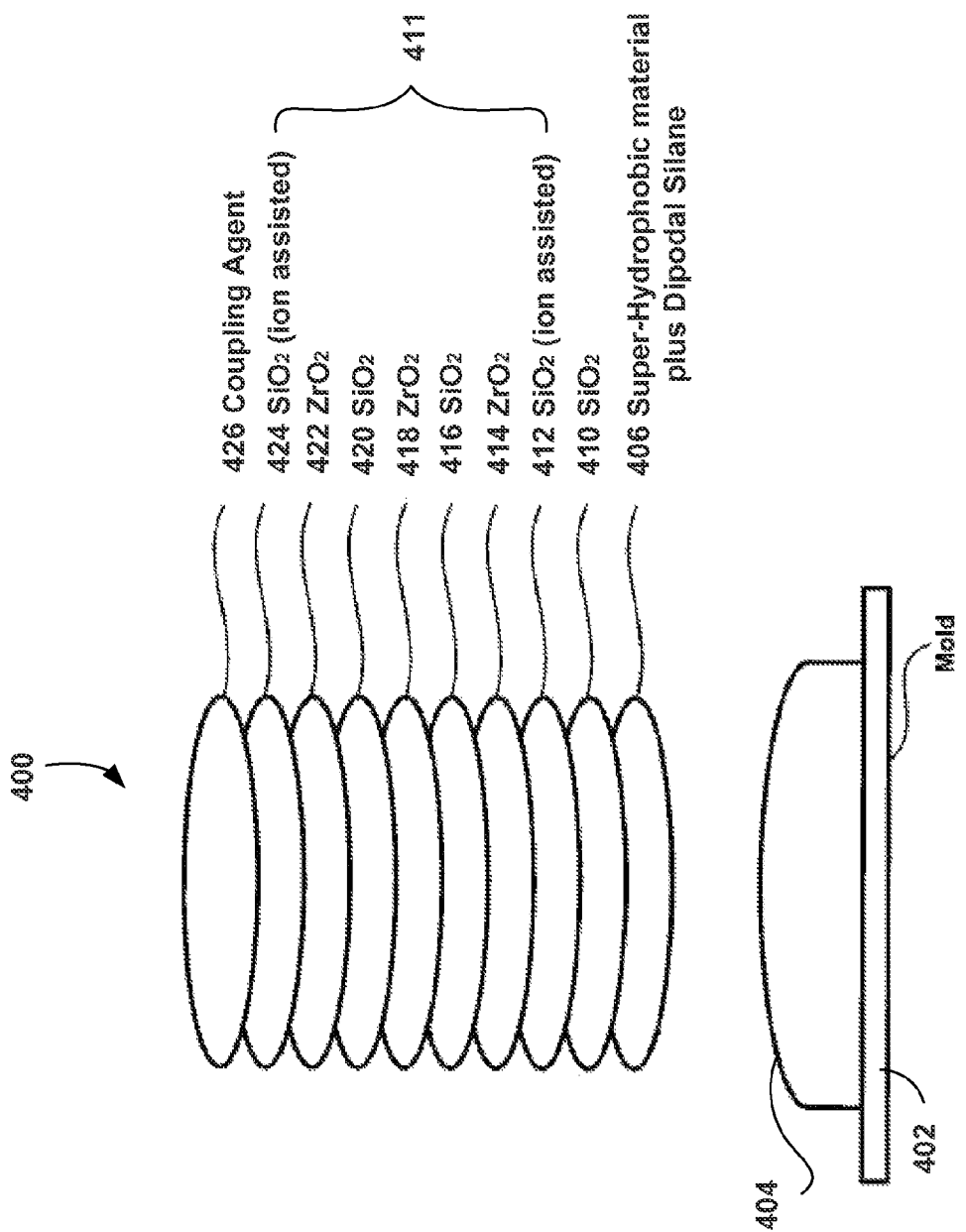
FIG. 4 shows preparation of an anti-reflective coated lens mold according to one embodiment of the present invention.

Referring now to FIG. 4, the processes described below are performed with a standard box coater and an electron beam for evaporation in connection with a mold 402 having an optical surface 404. The processes are done using well known vacuum practices.

Procedure:

(1) Cleaning the optical surface 404 of the mold 402. In one embodiment of the present invention, plasma cleaning is performed on the mold surface for about 2 min.

(2) Forming a layer 406 of a super hydrophobic material with a thickness of about 30 to 40 nm over the optical surface 404, where the super hydrophobic material contains about 1.7-8.3% of dipodal silane by weight. In one embodiment, the super hydrophobic material is contained within one or more crucibles in contact with a metal plate or boat. In certain embodiments, the super hydrophobic material is evaporated in vacuo from the one or more crucibles while heating the metal boat to a temperature between about 200° C. and about 500° C. In some embodiments, the crucible is a copper material and the boat is a stainless steel material.

(3) Forming a layer 410 of $SiO_2$ that is deposited without using ion assist and with a thickness of about 5 to 40 nm to the layer 406.

(4) Forming a layer 412 of $SiO_2$ that is deposited using ion assist and with a thickness of about 5 to 100 nm to the layer 410.

(5) Forming a layer 414 of $ZrO_2$ with a thickness of about 40 to 50 nm to the layer 412.

(6) Forming a layer 416 of $SiO_2$ that is deposited without using ion assist and with a thickness about 10 to 20 nm to the layer 414.

(7) Forming a layer 418 of $ZrO_2$ with a thickness of about 50 to 70 nm to the layer 416.

(8) Forming a layer 420 of $SiO_2$ that is deposited without using ion assist and with a thickness of about 25 to 40 nm to the layer 418.

(9) Forming a layer 422 of $ZrO_2$ with a thickness of about 10 to 25 nm to the layer 420.

(10) Forming a layer 424 of $SiO_2$ that is deposited using ion assist and with a thickness of about 5 to 15 nm to the layer 422.

(11) Forming a layer 426 of a coupling agent that is deposited using dip coating or vapor deposition and with a monolayer thickness to the layer 424.

It is noted that in this embodiment, the layer 406 of the super hydrophobic material contains about 1.7-8.3% of dipodal silane by weight relative to the super hydrophobic material so that the AR coating can be stable. An example of the concentration of dipodal silane in the super hydrophobic is that every 0.6 g of super hydrophobic material contains about 0.01 g to 0.05 g of dipodal silane. If no or too little dipodal silane is used in the super hydrophobic material, the AR coating crazes and separates from the mold. Moreover, layer 410 of $SiO_2$ functions as a protective seal to the AR layered structure 511 and also as natural bonding surface or a "link" between the AR layered structure 511 and the layer 406 of a super hydrophobic material. Likewise, layer 424 of $SiO_2$ provides a natural bonding surface or "link" between the AR layered structure 511 and the layer 426 of the coupling agent. It is noted that although layer 410 and layer 412 both are formed of $SiO_2$, they are formed with different processes such that they adhere to each other but function differently.

Example 5

Preparation of an AR Coating that is Applied to a Disposable Mold

In this Example, among other things, a process of applying an AR coating to a disposable mold is provided according to a further embodiment of the present invention. It is noted that in this Example, $SiO_2$ layers are formed or deposited with or without ion assist.

Figure 5:
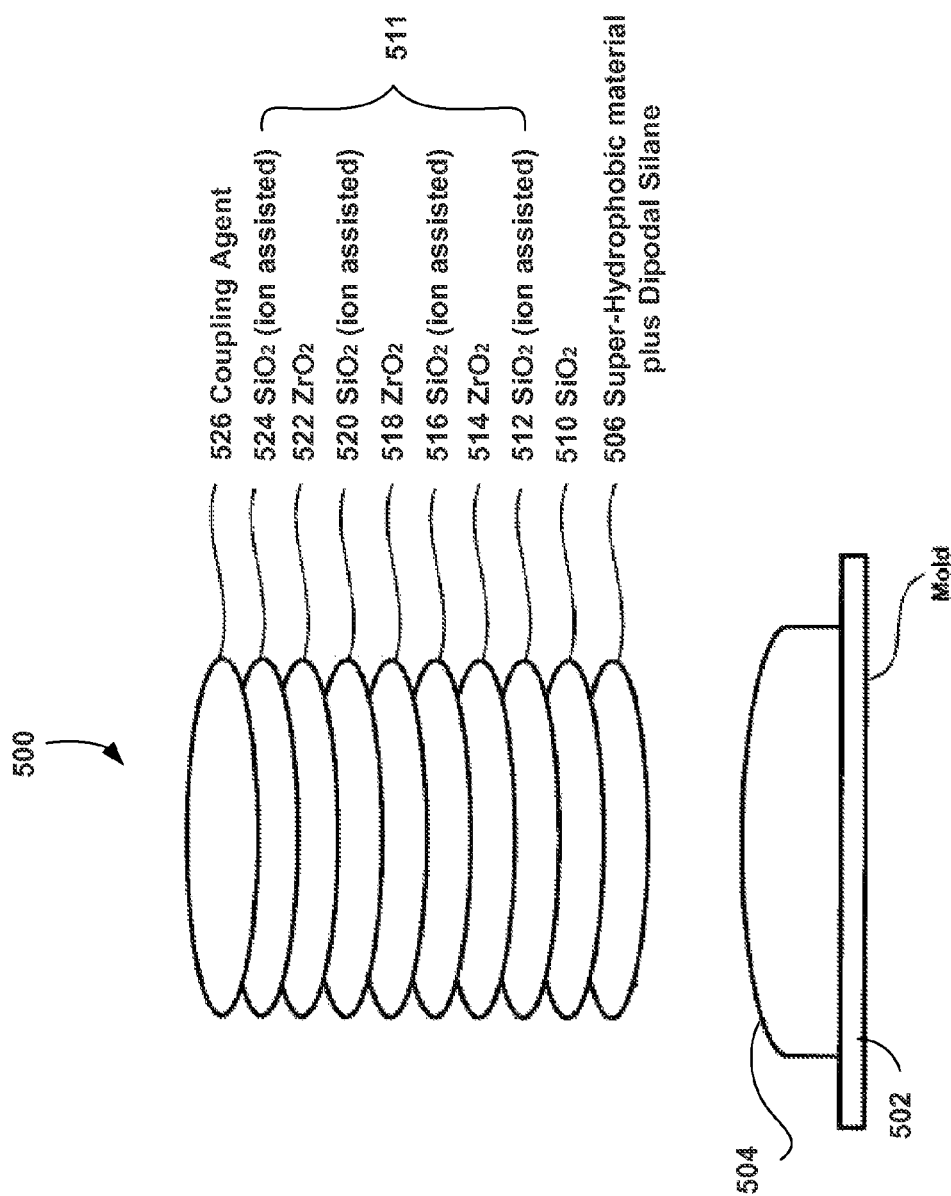
FIG. 5 shows preparation of an anti-reflective coated lens mold according to one embodiment of the present invention.

Referring now to FIG. 5, the processes described below are performed with a standard box coater and an electron beam for evaporation in connection with a mold 502 having an optical surface 504. The processes are done using well known vacuum practices.

Procedure:

(1) Cleaning the optical surface 504 of the mold 502. In one embodiment of the present invention, plasma cleaning is performed on the mold surface for about 2 min.

(2) Forming a layer 506 of a super hydrophobic material with a thickness of about 30 to 40 nm over the optical surface 504, where the super hydrophobic material contains about 1.7-8.3% of dipodal silane by weight relative to the super hydrophobic material. In one embodiment, the super hydrophobic material is contained within one or more crucibles in contact with a metal plate or boat. In certain embodiments, the super hydrophobic material is evaporated in vacuo from the one or more crucibles while heating the metal boat to a temperature between about 200° C. and about 500° C. In some embodiments, the crucible is a copper material containing steel wool, and the boat is a stainless steel material.

(3) Forming a layer 510 of $SiO_2$ that is deposited without using ion assist and with a thickness of about 5 to 40 nm to the layer 506.

(4) Forming a layer 512 of $SiO_2$ that is deposited using ion assist and with a thickness of about 5 to 100 nm to the layer 510.

(5) Forming a layer 514 of $ZrO_2$ with a thickness of about 40 to 50 nm to the layer 512.

(6) Forming a layer 516 of $SiO_2$ that is deposited using ion assist and with a thickness about 10 to 20 nm to the layer 514.

(7) Forming a layer 518 of $ZrO_2$ with a thickness of about 50 to 70 nm to the layer 516.

(8) Forming a layer 520 of $SiO_2$ that is deposited using ion assist and with a thickness of about 25 to 40 nm to the layer 518.

(9) Forming a layer 522 of $ZrO_2$ with a thickness of about 10 to 25 nm to the layer 520.

(10) Forming a layer 524 of $SiO_2$ that is deposited using ion assist and with a thickness of about 5 to 15 nm to the layer 522.

(11) Forming a layer 526 of a coupling agent that is deposited using vapor deposition and with a monolayer thickness to the layer 524.

Example 6

Preparation and Application of Coupling Agent

In Examples 4 and 5, among other things, the present invention is practiced with a layer of a coupling agent that is applied to the AR-coated mold to promote adhesion of the hard coating.

Material-wise, the coupling agents are functional silanes in which the silane bonds to the AR coating and the functional group bonds with the organic hard coat. According to one embodiment of the present invention, cyclic azasilanes are particularly well suited for the application, as they will form silane bonds at room temperature via a ring-opening reaction. This results in a monolayer with functional groups that readily attach to the hard coat, forming a strong AR to hardcoat bond. It is believed that it is the first time in the industry and only by the inventive discovery of the present invention, that cyclic azasilanes are utilized in an optical lens forming process as coupling agents. In another embodiment, the functional silane is a dipodal silane. For embodiments as shown in FIGS. 4 and 5, where $SiO_2$ is used as the first material with first index of refraction, bis(trimethoxysilylpropyl)amine is utilized as a silane coupling agent, resulting in a strong AR-to-hard-coat bond and making on-site AR lens formation a reality.

Procedure-wise, the coupling agent must be applied under aprotic conditions and can be done using many of the methods commonly practiced in the lens industry today, such as spin, spray, dip, and vacuum coating. Three specific examples of coupling agent application are provided below.

A. Vacuum Coating—Procedure:

(1) A pair of optical molds comprising a front mold and a back mold, where corresponding optical surfaces of the molds are AR-coated molds according to one of various embodiments of the present invention as illustrated in Examples 4 and 5, is placed in a vacuum chamber, which is evacuated to create an aprotic environment with a predetermined pressure, in which a coupling agent will vaporize when introduced into the chamber.

(2) The coupling agent is introduced into the sealed chamber and allowed to coat and react with each AR coating for a minimum of 10 minutes.

(3) The chamber is evacuated to the original (pre-coupling agent), predetermined pressure to remove excess coupling agent.

(4) The vacuum is released and the optical mold assembly is removed from the chamber. Afterwards, a hard coat can be applied.

B. Dip Coating—Procedure:

(1) A solution of coupling agent in an aprotic solvent is prepared (0.05% minimum). Examples of aprotic solvents include toluene, benzene, petroleum ether, or other hydrocarbon solvents.

(2) An AR-coated mold, prepared according to one of various embodiments of the present invention as illustrated in Examples 4 and 5, is exposed to (or treated with) the solution for a minimum of 5 minutes at room temperature.

(3) The treated mold is removed from the solution and rinsed with ethanol or a similar solvent.

(4) The mold is then air-dried and afterwards a hard coat can be applied.

C. Spin Coating—Procedure:

(1) A solution of coupling agent in an aprotic solvent is prepared (0.05% minimum). Examples of aprotic solvents include toluene, benzene, petroleum ether, Isopar L, or other hydrocarbon solvents.

(2) The solution is placed into a spin-coating system, wherein a pump or pressure chamber is used to spray the solution onto a rapidly rotating spindle.

(3) An AR-coated mold, prepared according to one of various embodiments of the present invention as illustrated in Examples 4 and 5, is placed on the spindle. The coupling agent solution is applied while the mold is rotating, creating an even coating.

(4) The treated mold is removed from the spindle and dried under IR heat. Hard coat can then be applied.

Example 7

Procedure for Making an AR-Coated Lens

This example shows a method or procedure of making an AR-coated lens according to one embodiment of the present invention.

The corresponding optical surfaces of a front mold and a back mold of an optical mold assembly were AR-coated according to the one embodiment of the present invention illustrated in one of Examples 4 and 5. A layer (426, 526) of a coupling agent consisting of or having N-n-butyl-aza-2,2-dimethoxy-silacyclopentane was then formed onto the AR surfaces (424, 524) using a dip coating method as set forth above in Example 6. A solution was prepared of 0.05% coupling agent in petroleum ether. The optical surfaces were submerged in the solution for 5 minutes at room temperature. They were then rinsed with ethanol, allowed to air-dry, and immediately hard-coated using a spin-coating process. Upon casting, the hard coat, AR, and super hydrophobic coatings transferred from the mold onto the lens.

In one aspect, the present invention relates to a method for applying an anti-reflective coating to an optical surface of a mold. In various embodiments of the present invention as shown in FIGS. 4 and 5, such a method has the steps of:

providing a lens mold 402 or 502 having an optical surface 404 or 504; forming a layer 406 or 506 of a super hydrophobic material with a thickness of about 20 to 100 nm over the optical surface 404 or 504, where the super hydrophobic material contains about 1.7-8.3% of dipodal silane by weight relative to the super hydrophobic material;

forming an anti-reflective coating layered structure 411 or 511 over the super hydrophobic layer 406 or 506; and forming a layer 426 or 526 of a coupling agent that is deposited using dip coating, spin coating or vapor deposition and with a monolayer thickness over the anti-reflective coating layered structure 411 or 511.

In one embodiment, the super hydrophobic material is contained within one or more crucibles in contact with a metal plate or boat. In certain embodiments, the super hydrophobic material is evaporated in vacuo from the one or more crucibles while heating the metal boat to a temperature between about 200° C. and about 500° C. In some embodiments, the crucible is a copper material and the boat is a stainless steel material.

The step of forming an anti-reflective coating layered structure 411 or 511 over the layer 408 or 508 can be performed with the steps of:

(1) forming a first layer 412, 512 or 612 of a first material with a first index of refraction and a thickness of about 5 to 100 nm, on the super hydrophobic layer 406 or 506;

(2) forming a second layer 414 or 514 of a second material with a second index of refraction and a thickness of about 40 to 50 nm, on the first layer 412 or 512;

(3) forming a third layer 416 or 516 of the first material with the first index of refraction and a thickness about 10 to 20 nm, on the second layer 414 or 514;

(4) forming a fourth layer 418 or 518 of the second material with second index of refraction and a thickness of about 50 to 70 nm, to the third layer 416 or 516;

(5) forming a fifth layer 420 or 520 of the first material with the first index of refraction and a thickness of about 25 to 40 nm, to the fourth layer 418 or 518;

(6) forming a sixth layer 422 or 522 of the second material with the second index of refraction and a thickness of about 10 to 25 nm, to the fifth layer 420 or 520; and (7) forming a seventh layer 424 or 524 of the first material with the first index of refraction and a thickness of about 5 to 15 nm, to the sixth layer 422 or 522.

In one embodiment, the first index of refraction and the second index of refraction satisfy a ratio of H/L>1, where L and H are values of the first and second index of refraction, respectively. In other words, the value of the second index of refraction is greater than the value of the first index of refraction.

In one embodiment, the first material with first index of refraction comprises $SiO_2$, and the second material with second index of refraction comprises $ZrO_2$.

In practicing the present invention according to the methods set forth above, each layer of $SiO_2$ is deposited using ion assist or without using ion assist.

In embodiments as shown in FIGS. 4 and 5, prior to the step of forming an anti-reflective coating layered structure 411 or 511 over the super hydrophobic layer 406 or 506, a step of forming a layer 410, 510 of $SiO_2$ that is deposited without ion assist and with a thickness of 5 to 40 nm over the super hydrophobic layer 406, 506 is performed such that the $SiO_2$ layer 410, 510 is formed between the super hydrophobic layer 506, 606 and the first layer 412, 512.

In one embodiment, the dipodal silane can be bis(trimethoxysilylpropyl)amine.

In one embodiment, the layer of the coupling agent is formed of a composition that comprises cyclic azasilanes. In one particular embodiment, the layer of the coupling agent is formed of N-n-butyl-aza-2,2-dimethoxy-silacyclopentane. In another embodiment, the layer of the coupling agent is formed of a composition that comprises dipodal silane.

In another aspect, the present invention relates to a mold with an optical surface having an anti-reflective coating that is transferable to an optical surface of a lens. In various embodiments as shown in FIGS. 4 and 5, such a mold has a layer 406 or 506 of a super hydrophobic material with a thickness of about 20 to 100 nm deposited over an optical surface 404 or 504 of the mold 402 or 502, where the super hydrophobic material contains about 1.7-8.3% of dipodal silane by weight relative to the super hydrophobic material. In one embodiment, the super hydrophobic material is contained within one or more crucibles in contact with a metal plate or boat. In certain embodiments, the super hydrophobic material is evaporated in vacuo from the one or more crucibles while heating the metal boat to a temperature between about 200° C. and about 500° C. In some embodiments, the crucible is a copper material and the boat is a stainless steel material.

The mold also has an anti-reflective coating layered structure 411 or 511 deposited over the super hydrophobic layer 406 or 506; and a layer 426 or 526 of a coupling agent that is deposited using dip coating or vapor deposition and with a monolayer thickness deposited over the anti-reflective coating layered structure 411 or 511.

As shown in FIGS. 4 and 5, the anti-reflective coating layered structure 411 or 511 has:

(1) a first layer 412 or 512 of a first material with a first index of refraction and a thickness of about 5 to 100 nm deposited over the super hydrophobic layer 406 or 506;

(2) a second layer 414 or 514 of a second material with a second index of refraction and a thickness of about 40 to 50 nm, deposited to the first layer 412 or 512;

(3) a third layer 416 or 516 of the first material with the first index of refraction and a thickness about 10 to 20 nm, deposited to the second layer 414 or 514;

(4) a fourth layer 418 or 518 of the second material with the second index of refraction and a thickness of about 50 to 70 nm, deposited to the third layer 416 or 516;

(5) a fifth layer 420 or 520 of the first material with the first index of refraction and a thickness of about 25 to 40 nm, deposited to the fourth layer 418 or 518;

(6) a sixth layer 422 or 522 of the second material with the second index of refraction and a thickness of about 10 to 25 nm, deposited to the fifth layer 420 or 520; and (7) a seventh layer 424 or 524 of the first material with the first index of refraction and a thickness of about 5 to 15 nm, deposited to the sixth layer 422 or 522.

The first index of refraction and the second index of refraction satisfy a ratio of H/L>1, wherein L and H are values of the first and second index of refraction, respectively. In other words, the value of the second index of refraction is greater than the value of the first index of refraction.

In one embodiment, the first material with first index of refraction comprises $SiO_2$, and the second material with second index of refraction comprises $ZrO_2$.

Each layer of $SiO_2$ in the anti-reflective coating layered structure is deposited using ion assist or without using ion assist.

In various embodiments as shown in FIGS. 4 and 5, alternatively, a layer 410, 510 of $SiO_2$ is deposited without ion assist and with a thickness of 5 to 40 nm over the layer 406, 506 such that the layer 410, 510 is formed between the layer 406, 506 and the layer 412, 512.

The dipodal silane can be bis(trimethoxysilylpropyl)amine.

The layer of coupling agent is formed of a composition that comprises a functional silane. The functional silane comprises dipodal silanes in some embodiments. In other embodiments the functional silane comprises cyclic azasilanes. In various embodiments as shown in FIGS. 4 and 5, the layer of coupling agent is formed of N-n-butyl-aza-2,2-dimethoxy-silacyclopentane.

In a further aspect, the present invention relates to an optical lens. The optical lens has a lens body with an optical surface and an anti-reflective coating formed on the optical surface, where in various embodiments as shown in FIGS. 4 and 5, the anti-reflective coating has a layer 406 or 506 of a super hydrophobic material with a thickness of about 20 to 100 nm deposited over an optical surface 404 or 504 of the mold 402 or 502, where the super hydrophobic material contains about 1.7-8.3% of dipodal silane by weight relative to the super hydrophobic material. In one embodiment, the super hydrophobic material is contained within one or more crucibles in contact with a metal plate or boat. In certain embodiments, the super hydrophobic material is evaporated in vacuo from the one or more crucibles while heating the metal boat to a temperature between about 200° C. and about 500° C. In some embodiments, the crucible is a copper material and the boat is a stainless steel material.

The anti-reflective coating also has an anti-reflective coating layered structure 411 or 511 deposited over the super hydrophobic layer 406 or 506; and a layer 426 or 526 of a coupling agent that is deposited using vapor deposition and with a monolayer thickness deposited over the anti-reflective coating layered structure 411 or 511 and coupled to the optical surface of the lens body.

The anti-reflective coating layered structure 411 or 511 is formed with:

(1) a first layer 412 or 512 of a first material with a first index of refraction and a thickness of about 5 to 100 nm deposited over the super hydrophobic layer 406 or 506;

(2) a second layer 414 or 514 of a second material with a second index of refraction and a thickness of about 40 to 50 nm, deposited to the first layer 412 or 512;

(3) a third layer 416 or 516 of the first material with the first index of refraction and a thickness about 10 to 20 nm, deposited to the second layer 414 or 514;

(4) a fourth layer 418 or 518 of the second material with the second index of refraction and a thickness of about 50 to 70 nm, deposited to the third layer 416 or 516;

(5) a fifth layer 420 or 520 of the first material with the first index of refraction and a thickness of about 25 to 40 nm, deposited to the fourth layer 418 or 518;

(6) a sixth layer 422 or 522 of the second material with the second index of refraction and a thickness of about 10 to 25 nm, deposited to the fifth layer 420 or 520; and (7) a seventh layer 424 or 524 of the first material with the first index of refraction and a thickness of about 5 to 15 nm, deposited to the sixth layer 422 or 522 and being in contact with the layer 426 or 526 of the coupling agent.

The first index of refraction and the second index of refraction satisfy a ratio of H/L>1, where L and H are values of the first and second index of refraction, respectively. In other words, the value of the second index of refraction is greater than the value of the first index of refraction.

In one embodiment, the first material with first index of refraction comprises $SiO_2$, and the second material with second index of refraction comprises $ZrO_2$.

Each layer of $SiO_2$ in the anti-reflective coating layered structure is deposited using ion assist or without using ion assist.

In various embodiments as shown in FIGS. 4 and 5, alternatively, a layer 410, 510 of $SiO_2$ is deposited without ion assist and with a thickness of 5 to 40 nm over the layer 406, 506 such that the layer 410, 510 is formed between the layer 406, 506 and the first layer 412, 512.

The dipodal silane can be bis(trimethoxysilylpropyl) amine.

The layer of coupling agent is formed of a composition that comprises cyclic azasilanes. In various embodiments as shown in FIGS. 4 and 5, the layer of coupling agent is formed of N-n-butyl-aza-2,2-dimethoxy-silacyclopentane.

Figure 2:
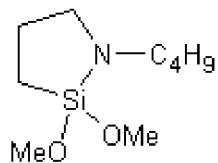
FIG. 2 shows chemical reactions related to coupling agents utilized for manufacturing an anti-reflective coated lens according to one embodiment of the present invention.
Figure 2:
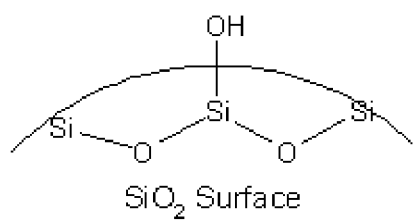
Figure 2:
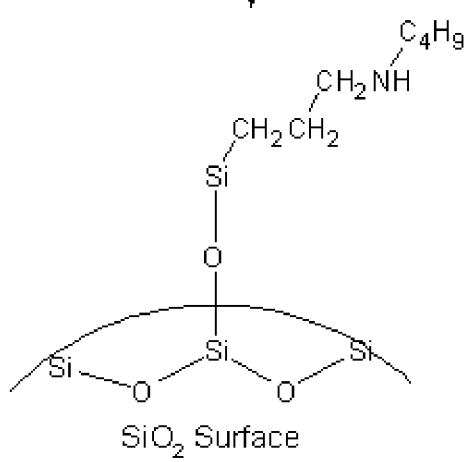

In yet another aspect, the present invention relates to a coupling agent usable in lens making. In one embodiment, the coupling agent comprises dipodal silanes. In one embodiment, the coupling agent comprises cyclic azasilanes. In one specific embodiment, cyclic azasilanes comprise N-n-butyl-aza-2,2-dimethoxy-silacyclopentane. It is noted that in use, cyclic azasilanes and dipodal silanes are applied in a solvent. For embodiments as shown in FIGS. 4 and 5, where $SiO_2$ is used as the first material with the first index of refraction, utilizing N-n-butyl-aza-2,2-dimethoxy-silacyclopentane as a coupling agent allows a surface bonding ring opening reaction without requiring water or heat, as shown in FIG. 2, resulting in much better bonding and making on-site AR lens formation a reality. This is much better than the process shown in FIG. 1, which requires high heat, among other things.

It is further noted that in practicing the present invention, the steps for each embodiment given above can be performed in the sequence as given, or in different orders.

In a further aspect, the present invention relates to an optical lens. In one embodiment, the optical lens has a lens body with an optical surface, a hard coat layer over the optical surface, and an anti-reflective coating over the optical surface.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A mold with an optical surface having an anti-reflective coating that is transferable to a lens, comprising:
    (a) a layer of a super hydrophobic material formed over the optical surface, by heating a thermal boat that is in contact with one or more crucibles containing the super hydrophobic material to a temperature between about 200° C. and about 500° C., wherein the super hydrophobic material contains an amount of dipodal silane that is a relative percentage of the super hydrophobic material;
    (b) an anti-reflective coating layered structure formed over the layer of the super hydrophobic material; and
    (c) a layer of a coupling agent deposited with a monolayer thickness to the anti-reflective coating layered structure using vapor deposition under aprotic conditions or by dip coating or spin coating using a solution of a coupling agent in an aprotic solvent; and
    (d) a scratch resistant hard coating,
    wherein an amount of the dipodal silane is effective to prevent the anti-reflective coating layered structure from crazing.

2. The mold of claim 1, wherein the amount of the dipodal silane is about 1.7-8.3% of the super hydrophobic material by weight.

3. The mold of claim 1, wherein the anti-reflective coating layered structure comprises:
    (a) a first layer of a first material with a first index of refraction and a thickness of about 5 to 100 nm, formed on the layer of the super hydrophobic material;
    (b) a second layer of a second material with a second index of refraction that is higher than the first index of refraction and a thickness of about 40 to 50 nm, formed on the first layer;
    (c) a third layer of the first material with the first index of refraction and a thickness of about 10 to 20 nm, formed on the second layer;
    (d) a fourth layer of the second material with the second index of refraction and a thickness of about 50 to 70 nm, formed on the third layer;
    (e) a fifth layer of the first material with the first index of refraction and a thickness of about 25 to 40 nm, formed on the fourth layer;
    (f) a sixth layer of the second material with the second index of refraction and a thickness of about 10 to 25 nm, formed on the fifth layer; and
    (g) a seventh layer of the first material with the first index of refraction and a thickness of about 5 to 15 nm, formed on the sixth layer.

4. The mold of claim 3, wherein the first material with the first index of refraction is $SiO_2$, and the second material with the second index of refraction is $ZrO_2$.

5. The mold of claim 4, wherein each layer of $SiO_2$ is deposited using ion assist or without using ion assist.

6. The mold of claim 1, wherein the dipodal silane comprises bis(trimethoxysilylpropyl)amine.

7. The mold of claim 1, wherein the layer of the coupling agent is formed of a composition that comprises cyclic azasilanes, or dipodal silanes.

8. The mold of claim 7, wherein the layer of the coupling agent is formed of N-n-butyl-aza-2,2-dimethoxy-silacyclopentane.

9. The mold of claim 1, further comprising a layer of $SiO_2$ formed between the anti-reflective coating layered structure and the layer of the super hydrophobic material.

10. An optical lens manufactured with a mold having an optical surface, comprising:
    a lens body with an optical surface;
    a hard coat layer coated on the optical surface of the lens body; and
    an anti-reflective coating comprising:
    (a) a layer of a super hydrophobic material formed over the optical surface of the mold, by heating a thermal boat that is in contact with one or more crucibles containing the super hydrophobic material to a temperature between about 200° C. and about 500° C., wherein the super hydrophobic material contains an amount of dipodal silane that is a relative percentage of the super hydrophobic material;
(b) an anti-reflective coating layered structure formed over the layer of the super hydrophobic material; and
(c) a layer of a coupling agent deposited with a monolayer thickness to the anti-reflective coating layered structure,
wherein the hard coat layer is substantially in contact with the layer of the coupling agent of the anti-reflective coating and wherein an amount of the dipodal silane is effective to prevent the anti-reflective coating layered structure from crazing.

11. The optical lens of claim 10, wherein the amount of the dipodal silane is about 1.7-8.3% of the super hydrophobic material by weight.

12. The optical lens of claim 10, wherein the anti-reflective coating layered structure comprises:
(a) a first layer of a first material with a first index of refraction and a thickness of about 5 to 100 nm, formed on the layer of the super hydrophobic material;
(b) a second layer of a second material with a second index of refraction that is higher than the first index of refraction and a thickness of about 40 to 50 nm, formed on the first layer;
(c) a third layer of the first material with the first index of refraction and a thickness of about 10 to 20 nm, formed on the second layer;
(d) a fourth layer of the second material with the second index of refraction and a thickness of about 50 to 70 nm, formed on the third layer;
(e) a fifth layer of the first material with the first index of refraction and a thickness of about 25 to 40 nm, formed on the fourth layer;
(f) a sixth layer of the second material with the second index of refraction and a thickness of about 10 to 25 nm, formed on the fifth layer; and
(g) a seventh layer of the first material with the first index of refraction and a thickness of about 5 to 15 nm, formed on the sixth layer and being in contact with the layer of the coupling agent.

13. The optical lens of claim 12, wherein the first material with the first index of refraction is $SiO_2$, and the second material with the second index of refraction is $ZrO_2$.

14. The optical lens of claim 13, wherein each layer of $SiO_2$ is deposited using ion assist or without using ion assist.

15. The optical lens of claim 10, wherein the dipodal silane comprises bis(trimethoxysilylpropyl)amine.

16. The optical lens of claim 10, wherein the layer of the coupling agent is formed of a composition that comprises cyclic azasilanes, or dipodal silanes.

17. The optical lens of claim 16, wherein the layer of the coupling agent is formed of N-n-butyl-aza-2,2-dimethoxysilacyclopentane.

18. The optical lens of claim 10, further comprising a layer of $SiO_2$ formed between the anti-reflective coating layered structure and the layer of the super hydrophobic material.

19. A mold with an optical surface having an anti-reflective coating that is transferable to a lens, comprising:
(a) a layer of a super hydrophobic material formed over the optical surface, wherein the super hydrophobic material contains an amount of dipodal silane that is a relative percentage of the super hydrophobic material;
(b) an anti-reflective coating layered structure formed over the layer of the super hydrophobic material; and
(c) a layer of a coupling agent deposited with a monolayer thickness to the anti-reflective coating layered structure using vapor deposition under aprotic conditions or by dip coating or spin coating using a solution of a coupling agent in an aprotic solvent; and
(d) a scratch resistant hard coating,
wherein an amount of the dipodal silane is effective to prevent the anti-reflective coating layered structure from crazing.

20. The mold of claim 19, wherein the amount of the dipodal silane is about 1.7-8.3% of the super hydrophobic material by weight.

21. The mold of claim 19, wherein the anti-reflective coating layered structure comprises:
(a) a first layer of a first material with a first index of refraction formed on the layer of the super hydrophobic material;
(b) a second layer of a second material with a second index of refraction formed on the first layer;
(c) a third layer of the first material with the first index of refraction formed on the second layer;
(d) a fourth layer of the second material with the second index of refraction formed on the third layer;
(e) a fifth layer of the first material with the first index of refraction formed on the fourth layer;
(f) a sixth layer of the second material with the second index of refraction formed on the fifth layer; and
(g) a seventh layer of the first material with the first index of refraction formed on the sixth layer.

22. The mold of claim 21, wherein the first index of refraction and the second index of refraction satisfy a ratio of H/L >1, wherein L and H are values of the first and second index of refraction, respectively.

23. The mold of claim 22 wherein the first material with the first index of refraction is $SiO_2$, and the second material with the second index of refraction is $ZrO_2$.

24. The mold of claim 19, wherein the layer of coupling agent is formed of a composition that comprises cyclic azasilanes, or dipodal silanes.

25. The mold of claim 19, wherein the layer of super hydrophobic material is formed over the optical surface by heating a thermal boat is in contact with one or more crucibles containing the super hydrophobic material, at a temperature.

26. The mold of claim 25, wherein the temperature is between about 200° C. and about 500° C.

27. An optical lens manufactured with a mold having an optical surface, comprising:
a lens body with an optical surface;
a hard coat layer coated on the optical surface of the lens body; and
an anti-reflective coating comprising:
(a) a layer of a super hydrophobic material formed over the optical surface of the mold, wherein the super hydrophobic material contains an amount of dipodal silane that is a relative percentage of the super hydrophobic material;
(b) an anti-reflective coating layered structure formed over the layer of the super hydrophobic material; and
(c) a layer of a coupling agent deposited with a monolayer thickness to the anti-reflective coating layered structure,
wherein the hard coat layer is substantially in contact with the layer of the coupling agent of the anti-reflective coating and wherein an amount of the dipodal silane is effective to prevent the anti-reflective coating layered structure from crazing.

28. The optical lens of claim 27, wherein the amount of the dipodal silane is about 1.7-8.3% of the super hydrophobic material by weight.

29. The optical lens of claim 27, wherein the anti-reflective coating layered structure comprises:
  (a) a first layer of a first material with a first index of refraction formed on the layer of the super hydrophobic material;
  (b) a second layer of a second material with a second index of refraction formed on the first layer;
  (c) a third layer of the first material with the first index of refraction formed on the second layer;
  (d) a fourth layer of the second material with the second index of refraction formed on the third layer;
  (e) a fifth layer of the first material with the first index of refraction L and a thickness of about 25 to 40 nm, formed on the fourth layer;
  (f) a sixth layer of the second material with the second index of refraction formed on the fifth layer; and
  (g) a seventh layer of the first material with the first index of refraction formed on the sixth layer and being in contact with the layer of the coupling agent.

30. The optical lens of claim 29, wherein the first index of refraction and the second index of refraction satisfy a ratio of H/L >1, wherein L and H are values of the first and second index of refraction, respectively.

31. The optical lens of claim 30, wherein the first material with the first index of refraction is $SiO_2$, and the second material with the second index of refraction is $ZrO_2$.

32. The optical lens of claim 27, wherein the layer of the coupling agent is formed of a composition that comprises cyclic azasilanes, or dipodal silanes.

33. The optical lens of claim 27, wherein the layer of the super hydrophobic material is formed over the optical surface of the mold by heating a thermal boat that is in contact with one or more crucibles containing the super hydrophobic material, at a temperature.

34. The optical lens of claim 33, wherein the temperature is between about 200° C. and about 500° C.

* * * * *